United States Patent [19]

Odeh

[11] Patent Number: 4,638,447
[45] Date of Patent: Jan. 20, 1987

[54] METHOD FOR DETERMINING CONSISTENT OIL RELATIVE PERMEABILITY VALUES FROM DYNAMIC DISPLACEMENT DATA

[75] Inventor: Aziz S. Odeh, Plano, Tex.

[73] Assignee: Mobil Oil Corporation, New York, N.Y.

[21] Appl. No.: 544,175

[22] Filed: Oct. 21, 1983

[51] Int. Cl.[4] .............................................. G01N 15/08
[52] U.S. Cl. .................................... 364/556; 364/422; 73/38
[58] Field of Search ............... 364/552, 556, 420, 421, 364/422; 73/38; 166/250, 252

[56] References Cited

U.S. PATENT DOCUMENTS

| 2,437,935 | 3/1948 | Brunner et al. | 73/38 |
| 2,737,804 | 3/1956 | Herzog et al. | 73/38 |
| 4,506,542 | 3/1985 | Rose | 73/38 |

OTHER PUBLICATIONS

"Some Physical Characteristics of Oil Sands", by G. Fancher et al, published in the Pennsylvania State College Bulletin, State College, Pa., May 1933.
"Relative Permeability Measurements on Small Core Samples", by Morris, R. H. et al., The Procedures Monthly, pp. 19-25, Aug. 1947.
"A Simplified Method for Computing Oil Recovery by Gas or Water Drive", by Wedge, H. J., Transactions, AIME, vol. 195, pp. 91-98, 1952.
"Calculation of Relative Permeability From Displacement Experiments", by Johnson, E. F. et al., Transactions, AIME, vol. 216, pp. 370-372, 1959.
"Graphical Techniques for Determining Relative Permeability From Displacement Experiments", by Jones, S. C. et al., Transactions, AIME, vol. 265, pp. 807-817, May 1978.
"Laboratory Determination of Relative Permeability", Richardson, J. G. et al., Transactions, AIME, vol. 195, pp. 187-196, 1952.

Primary Examiner—Parshotam S. Lall
Attorney, Agent, or Firm—Alexander J. McKillop; Michael G. Gilman; Charles J. Speciale

[57] ABSTRACT

Corrected oil relative permeability values for a core sample are determined from dynamic displacement measurements by the steps of plotting a ratio of oil rate output ($q_o$) to calculated oil relative permeability values ($k_{ro}$) vs. average water saturation ($\bar{S}_w$), determining if a straight line segment exists in areas of the plot corresponding to high average oil saturations, and if it does, extrapolating the straight line segment to the end of the plotted data, otherwise plotting a tangent curve from a beginning point of the plot, and correcting the calculated oil relative permeability values $K_{ro}$ by mulitplying the calculated values $k_{ro}$ by a ratio of a value on the $q_o/k_{ro}$ plot to a value on the extrapolated line or constructed tangent curve at the same average water saturation value. The applied corrections eliminate distortions in the calculated oil relative permeability values $k_{ro}$ due to an end effect at the core sample which causes distortions in the dynamic displacement measurements.

7 Claims, 10 Drawing Figures

METHOD FOR DETERMINING CONSISTENT OIL RELATIVE PERMEABILITY VALUES FROM DYNAMIC DISPLACEMENT DATA

CROSS-REFERENCE TO RELATED APPLICATION

The present invention is related to subject matter disclosed and claimed in U.S. Application Ser. No. 544,176, filed on even date herewith and assigned to the same assignee as the present invention.

BACKGROUND OF THE INVENTION

1. Field of the Invention

The present invention relates to a method for determining consistent oil relative permeability values ($k_{ro}$) from dynamic displacement measurements conducted on a subsurface core sample.

2. Discussion of the Prior Art

Oil relative permeability values are used in a number of significant ways in many oil reservoir engineering calculations. However, it is difficult to measure oil relative permeabilities in the laboratory on a core sample. Two techniques are typically used by the oil industry to obtain oil relative permeability values. The first is the so-called steady state method, which is described in the article entitled "Relative Permeability Measurements on Small Core Samples" by Morris, R. H. et al, *The Procedures Monthly*, pp. 19–25, August, 1947. The other method is the dynamic displacement method, which is described in the following articles: "A Simplified Method for Computing Oil Recovery by Gas or Water Drive" by Wedge, H. J., *Transactions*, AIME, Vol. 195, pp. 91–98, 1952; "Calculation of Relative Permeability From Displacement Experiments" by Johnson, E. F. et al, *Transactions*, AIME, Vol. 216, pp. 370–372, 1959; "Graphical Techniques for Determining Relative Permeability From Displacement Experiments" by Jones, S. C. et al, *Transactions*, AIME, Vol. 265, pp. 807–817, 1978. The latter article discloses a graphical technique for determining relative oil ($k_{ro}$) and water ($k_{rw}$) permeability values from dynamic displacement measurements, which technique will be hereinafter referred to as the Jones and Rozelle technique.

A significant problem with using a steady state technique to determine oil relative permeability values is that it is time consuming, as the steady state measurements required take considerable time for stabilization. Thus, a few days may be required for every data point of a plot of oil relative permeability vs. core saturation (water ($\bar{S}_w$) or oil ($\bar{S}_o$)) which is calculated in the technique and thus weeks are required to obtain a complete oil relative permeability curve.

In the dynamic displacement method of calculating oil relative permeability values, a small core sample is flooded with water to saturation and then flooded with oil to its irriducible water saturation. This cycle is repeated while the pressure drop across the core, and the oil and water production fractions, as a function of total oil and water injected (injection rate x time), are recorded. This data, together with oil and water viscosity, the absolute permeability of the core, and the core pore volume, are used to calculate oil relative permeability values ($k_{ro}$), as well as water relative permeability values ($k_{rw}$), as a function of saturation (oil or water) at the effluent end of the core. A greater appreciation of this conventional technique can be had by review of those above-referenced articles which discuss the dynamic displacement method.

The theory upon which interpretation of the dynamic displacement data rests and upon which oil relative permeability determinations are made assumes that the capillary pressure effects on the core saturation distribution are negligible. However, there is an observable pressure drop discontinuity near the effluent end of the core sample caused by capillary forces, which is known as the "end-effect". This resistance to effluent flow distorts the pressure drop data which are taken during a dynamic displacement test, causing consequent distortions in both relative oil and water permeability values determined from that data.

The so-called "end-effect" was perhaps first recognized by Richardson, et al and reported in the article entitled "Laboratory Determination of Relative Permeability", Richardson, J. G. et al, *Transactions*, AIME, Vol. 195, pp. 187–196; 1952. In this article, Richardson, et al report experimental results of a two-phase flow on a 30 centimeter long core sample cut into 8 sections. The sections were arranged perpendicular to the axis of the core and were machined and clamped together in a flow apparatus. Two-phase flow experiments were run at various flow rates and the saturation in each section was measured for each experiment. The results show that near the outflow or effluent end of a core sample, a zone exists where the wetting phase saturation increases rapidly and achieves a maximum value at the effluent face. Beyond this zone, towards the inflow end, the saturation is uniform. The width of the zone decreases with an increase in flow rate.

It appears from the results reported by Richardson, et al that a very high flow rate is required in the dynamic displacement tests to effectively remove the end zone and its effects on the dynamic displacement data used for determining relative oil and water permeability values. However, physical limitations on the experimental equipment used in the dynamic displacement measurements typically do not permit the high rates of flow which would be required to eliminate measurement perturbations caused by the end-effect. Moreover, it is difficult to determine a critical minimum flow rate which is required to eliminate these perturbations.

SUMMARY OF THE INVENTION

One object of the present invention is to provide a method for accurately determining oil relative permeability values from dynamic displacement measurements data. In particular, the invention is directed to a method in which oil relative permeability values are first calculated, using conventional techniques, such as, for example, the Jones and Roszelle graphical technique discussed above, from dynamic displacement measurement data, and then corrected to eliminate core end-effect perturbations. Thus, with the method of the invention, consistent oil relative permeability values can be obtained from dynamic displacement core sample measurement data, even when low fluid flow rates are used.

This object of the invention is achieved by first calculating oil relative permeability values $k_{ro}$ from dynamic displacement measurement data, using, for example, the Jones and Roszelle technique discussed above. Thereafter a ratio $q_o/k_{ro}$ is plotted against average water ($\bar{S}_w$) or oil ($\bar{S}_o$) saturation ($\bar{S}_w = 1 - \bar{S}_o$), where $q_o$ is the oil flow rate at the output end, that is, $q_o = f_o q_t$, where $f_o$ is the instantaneous oil fraction in the effluent leaving the core (a value between 0 and 1) and $q_t$ is the rate of oil injection into the core during an oil flood. In plotting $q_o/k_{ro}$, an initial starting point is selected which is a calculation of $k_{ro}$ at the residual water saturation of the core, using Darcy's Law. For this point, $f_o=1$ and the value $q_o/k_{ro}=q_t/k_{ro}$.

The plotted value $q_o/k_o$ vs. average water ($\bar{S}_w$) or oil ($\bar{S}_o$) saturation is then examined. It normally exhibits a straight line segment in the range of high oil saturation. This straight line segment is drawn and extrapolated to the limit of the experimental ($q_o/k_{ro}$) data obtained from the dynamic displacement experiments. For very low displacement rates, the straight line segment may not exist, in which a case a tangent is drawn to the curve of $q_o/k_{ro}$ vs. average core saturation (water $\bar{S}_w$ or oil $\bar{S}_o$), beginning at the point $q_t/k_{ro}$. Following this, corrected oil relative permeability values are calculated in accordance with the expression $k_{roc}=k_{ro}(q_o/k_{ro})/(q_o/k_{ro})SL$, where ($q_o/k_{ro}$) is the plotted $q_o/k_{ro}$ value using the oil relative permeability values $k_{ro}$ obtained from, e.g., the Jones and Roszelle technique, and ($q_o/k_{ro}$)SL is the plotted value read on the straight line or its extrapolation for the same average saturation value.

The value $k_{roc}$ is the corrected oil relative permeability value, which is used in the place of the conventionally calculated oil relative permeability values $k_{ro}$ to obtain a curve of oil relative permeability vs. saturation at the effluent end of the core sample.

The method of the invention, as well as the advantages thereof, will be more readily understood from the following detailed description which is provided in connection with the accompanying drawings.

DETAILED DESCRIPTION OF THE INVENTION

In taking dynamic displacement measurements and in subsequently calculating relative oil permeability values ($k_{ro}$) from the acquired data, it can be observed that oil relative permeability values ($k_{ro}$), calculated using conventional techniques, such as the Jones and Roszelle technique, are a strong function of the displacement rate ($q_t$), i.e., fluid flow rate, used in obtaining the dynamic displacement data. Variations in the calculated oil relative permeability values can be attributed to the so-called end-effect discussed above. Moreover, it can be observed that a critical fluid displacement rate ($q_t$) required to eliminate the end-effect over a wide range of saturation values is, for all practical purposes, unattainable. For example, various dynamic displacement experiments using water-oil systems were performed on several core samples, designated as 4929B, P$_2$, P$_7$ and P$_9$. Different displacement rates $q_t$ (e.g., 0.05, 0.15, 0.35 and 0.5 cc/min) were used for each core sample, and relative permeabilities to oil $k_{ro}$ were calculated using the Jones and Roszelle technique. Plots of oil relative permeability vs. water saturation $S_w$ were then produced and are shown in FIGS. 1, 5, 7 and 9.

Figure 1:
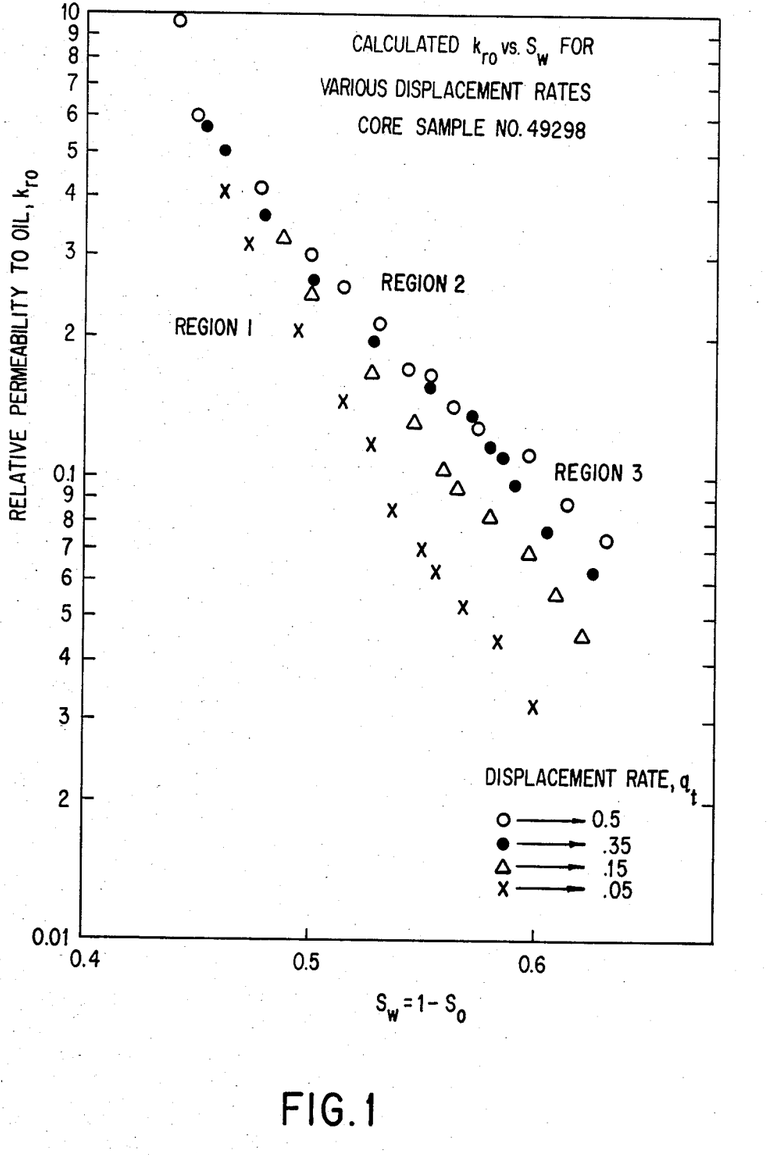
FIG. 1 are plots of calculated oil relative permeability values ($k_{ro}$) vs. water saturation ($S_w$), obtained using oil relative permeability values calculated in accordance with conventional techniques.

FIG. 1 is a representative of the results which were obtained. Three different regions (1, 2, 3) can be identified in the FIG. 1 plots, according to how great a deviation in plotted results occurred for different displacement rates $q_t$. At relatively high oil saturation (relatively low water saturation), the oil relative permeability values are, for all practical purposes, independent of displacement rate (flow rate). This is arbitrarily identified as region 1. At relatively low oil saturation (relatively high water saturation), oil relative permeability values are strong functions of flow rate and this region is identified as region 3 in FIG. 1. Between regions 1 and 3 is what is arbitrarily called a second region or transitional region, where the effects of flow rate on calculated permeability values $k_{ro}$ decreases as oil saturation increases. In regions 2 and 3 the calculated oil relative permeability values $k_{ro}$ decreased significantly with a decrease in the oil flow rate $q_t$. The deviations in obtained results are attributed to the end-effect discussed above, which causes an extra pressure drop at the effluent end of the core sample. The width of the end-effect zone increases with a decrease in flow rate, so that the additive pressure drop caused by it compared with the pressure drop due to the viscous forces will be relatively higher for low displacement rates. Since relative permeability, as calculated by the Jones and Roszelle technique, is basically inversely proportional to the pressure drop across the core, a low flow rate results in a calculated relative permeability value which is too low. The experimental results shown in FIG. 1 in region 1, where the calculated oil relative permeabilities do not vary significantly with displacement rate for a wide variation of rates, indicates that the effect of the extra pressure drop due to the end-effect zone must be negligible. Otherwise, the relative permeability values would continue to be a function of flow rates, as in region 3. The data depicted in FIG. 1 indicates that during an oil flood dynamic displacement experiment, there is a critical oil saturation where the end-effect becomes insignificant. This critical saturation increases with a decrease in rate.

Figure 2:
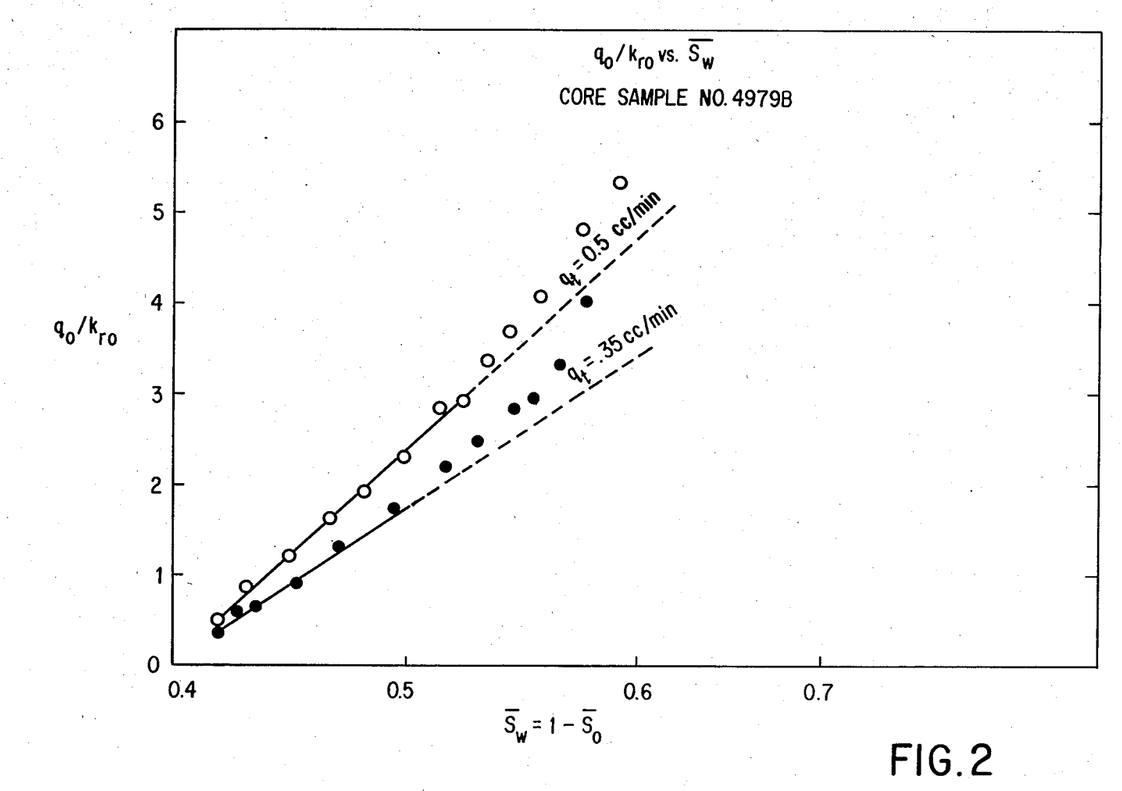
FIG. 2 is a plot of ($q_o/k_{ro}$) vs. average water saturation ($\bar{S}_w$) obtained using oil relative permeability values $k_{ro}$ calculated in accordance with conventional techniques and illustrating a portion of the method of the invention.

FIG. 2 shows plots of the ratio of oil output flow $q_o$ to calculated oil relative permeability $k_{ro}$ vs. the average water saturation ($\bar{S}_w$) for the core sample used in the FIG. 1 plots. An observation of this plot shows that a straight line segment is produced where the oil saturation is relatively high. Experimental results indicate that the range of oil saturation where the straight line persists increases with displacement rate, as also shown in FIG. 2. Thus, at very low flow rates, the straight line segment is extremely short or non-existent and the previously described region 1 in the relative permeability plot is absent. The deviation of the remaining points of the $q_o/k_{ro}$ vs. $\bar{S}_w$ plot from the extrapolation of the straight line increases with a decrease in oil saturation (an increase in water saturation). For the same oil saturation, the deviation decreases with an increase in displacement rate. Since at relatively high oil saturation the end-effect is insignificant, which coincides with the observed linear relationship between $q_o/k_{ro}$ vs. $\bar{S}_w$, the present invention is based on the theory that the straight line relationship should be the true relationship between the plot of $q_o/k_{ro}$ vs. $\bar{S}_w$ for the total range of oil saturation values were it not for the perturbations caused by the end-effect. In other words, the difference between the experimentally determined ratio $q_o/k_{ro}$ and the corresponding values read from the extrapolated straight line, reflects the perturbations introduced by the extra pressure drop caused by the end-effect.

In the method of the invention, the end-effect is corrected for by correcting the experimentally determined ratio $q_o/k_{ro}$ to the extrapolated straight line data.

In the method of the invention, the first step is to conduct conventional dynamic displacement tests using an oil and water flood, and from the data obtained, to calculate the relative permeability to oil ($k_{ro}$) of the core under consideration by the Jones and Roszelle technique described below and in more detail in the Jones and Roszelle article referenced above.

Briefly, and by way of background, the method of calculating oil relative permeability values using the Jones and Roszelle technique is as follows.

Relative oil ($k_{ro}$) and water ($k_{rw}$) permeability values are defined by the equations:

$$k_{ro} = u_o f_o / \lambda_2^{-1} \qquad (1)$$

and $$k_{rw} = u_w f_w / \lambda_2^{-1} \qquad (2)$$

where $u_o$ is the viscosity of the oil used in the dynamic displacement measurements, $u_w$ is the viscosity of water used in the dynamic displacement measurements, $f_o$ is the fraction of oil produced in the core effluent (0–100%; $f_o = 1 - f_w$), $f_w$ is the fraction of water produced in the core effluent (0–100%), and $\lambda_2^{-1}$ is an effective viscosity. The values $f_o$, $f_w$ and $\lambda_2^{-1}$ are determined as functions of core saturation.

The effective viscosity $\lambda_2^{-1}$ can be determined, per the Jones and Roszelle technique, by taking a tangent to a curve of average effective viscosity $\bar{\lambda}^{-1}$ vs. total injected fluid (rate x time) for particular values of injected fluid Qi (dimensioned in terms of pore volume), and extending the tangent line to the average effective viscosity $\bar{\lambda}^{-1}$ axis. This extension yields an effective viscosity value $\lambda_2^{-1}$, which can be used to solve equations (1) and (2) above. Mathematically, the tangent line which yields the effective viscosity $\lambda_2^{-1}$ is defined by $$\lambda_2^{-1} = \bar{\lambda}^{-1} - Qi \frac{d\bar{\lambda}^{-1}}{dQi} \qquad (3)$$

where Qi represents injected fluid in terms of core pore volume.

The average effective viscosity $\bar{\lambda}^{-1}$ values are in turn defined by the following relationship:

$$\bar{\lambda}^{-1} = u_b \left( \frac{\Delta P}{q} \right) / \left( \frac{\Delta P_b}{q_b} \right) \qquad (4)$$

where $\Delta P_b$ is the pressure drop across the core during a water-only steady state flood of the core sample, $q_b$ is the injection rate of the water, $u_b$ is the water viscosity, $\Delta P$ is the pressure drop across the core during an oil flood measurement and q is the oil injection rate. The average effective viscosity $\bar{\lambda}^{-1}$ obtained from equation (4) is plotted vs. the total amount of injected fluid Qi, given in terms of core pore volume, and the effective viscosity $\lambda_2^{-1}$ is then obtained, as described above, for any desired injected fluid amount Qi.

The other variables in equations (1) and (2) are $f_o$ and $f_w$. These are determined as follows:

$$f_o = \frac{\text{rate of oil produced}}{\text{rate of oil injection}} \qquad (5)$$

$$f_w = \frac{\text{rate of water produced}}{\text{rate of oil injection}} \qquad (6)$$

with the values $\lambda_2^{-1}$, $f_o$ and $f_w$, relative permeability values for oil ($k_{ro}$) and water ($k_{rw}$) can be determined from equations (1) and (2) above.

After oil relative permeability values $k_{ro}$ are calculated using, for example, the Jones and Roszelle technique, the ratio $q_o/k_{ro}$ vs. average water saturation $\bar{S}_w$ is plotted. In plotting $q_o/k_{ro}$ vs. $\bar{S}_w$, an initial oil relative permeability value $k_{roi}$ for the plotted curve is first determined using Darcy's law as follows:

$$q_o = \frac{A \cdot k \cdot k_{roi}}{u_o} \frac{\Delta P}{L} \qquad (7)$$

where $q_o$ is the core effluent rate, A is the cross-sectional area of the core sample, k is the specific permeability of the core (measured when only water or oil alone is present), $k_{roi}$ is a relative permeability to oil at residual water saturation, $u_o$ is the viscosity of oil, $\Delta P$ is the pressure drop across the core at residual water saturation, and L is the length of the core. All of the values in the above equation are fixed, except for $k_{roi}$, which can then be calculated. This provides an initial oil relative permeability starting point $k_{roi}$ for the plot $q_o/k_{ro}$. For this point, $f_o = 1$ and $q_o/k_{ro} = q_t/k_{roi}$.

After plotting the ratio $q_o/k_{ro}$ vs. $\bar{S}_w$ using the initial $k_{roi}$ point calculated from Darcy's law, the plot curve is evaluated. It normally will show a straight line segment in the range of high oil saturations. This straight line segment is then drawn and extrapolated to the limit of the experimental data, as shown in FIG. 2. For very low displacement rates, the straight line segment may not exist. If this occurs, the initial starting point, i.e., $q_t/k_{roi}$, is used at a beginning point and a tangent is drawn to the curve of the $q_o/k_{ro}$ ratio plot, as shown in FIG. 3.

Figure 3:
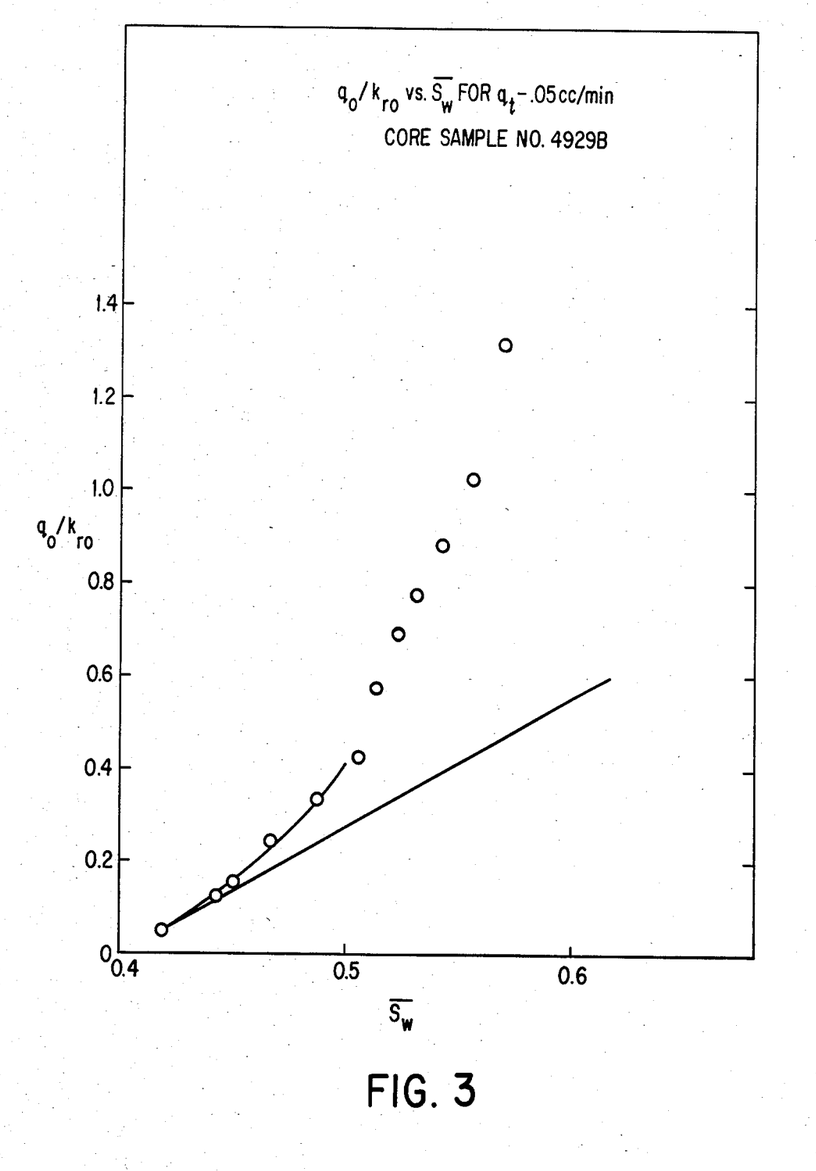
FIG. 3 is another plot of ($q_o/k_{ro}$) vs. average water saturation ($\bar{S}_w$) for a particular displacement rate ($q_t$) and further illustrating another portion of the method of the invention.

Once the extrapolated straight line or tangent curve is constructed, the corrected relative permeability values $k_{roc}$ can then be calculated in accordance with the expression:

$$k_{roc} = k_{ro}(q_o/k_{ro})/(q_o/k_{ro})SL \qquad (8)$$

where the value $(q_o/k_{ro})$ is the plotted value on the $q_o/k_{ro}$ vs. $\bar{S}_w$ curve, calculated using the Jones and Roszelle technique discussed above, and $(q_o/k_{ro})SL$ is the plotted value read on the straight line or its extrapolation, as shown in FIG. 2, or the tangent curve, as shown in FIG. 3, constructed in accordance with the invention for the same average water saturation $(\bar{S}_w)$ value.

The corrected values $k_{roc}$ for oil relative permeability are then used in place of conventionally calculated, e.g., Jones and Roszelle technique, $k_{ro}$ values to produce a curve of oil relative permeability vs. saturation ($k_{ro}$ vs. $S_w$) at the effluent end of the core samples.

Figure 4:
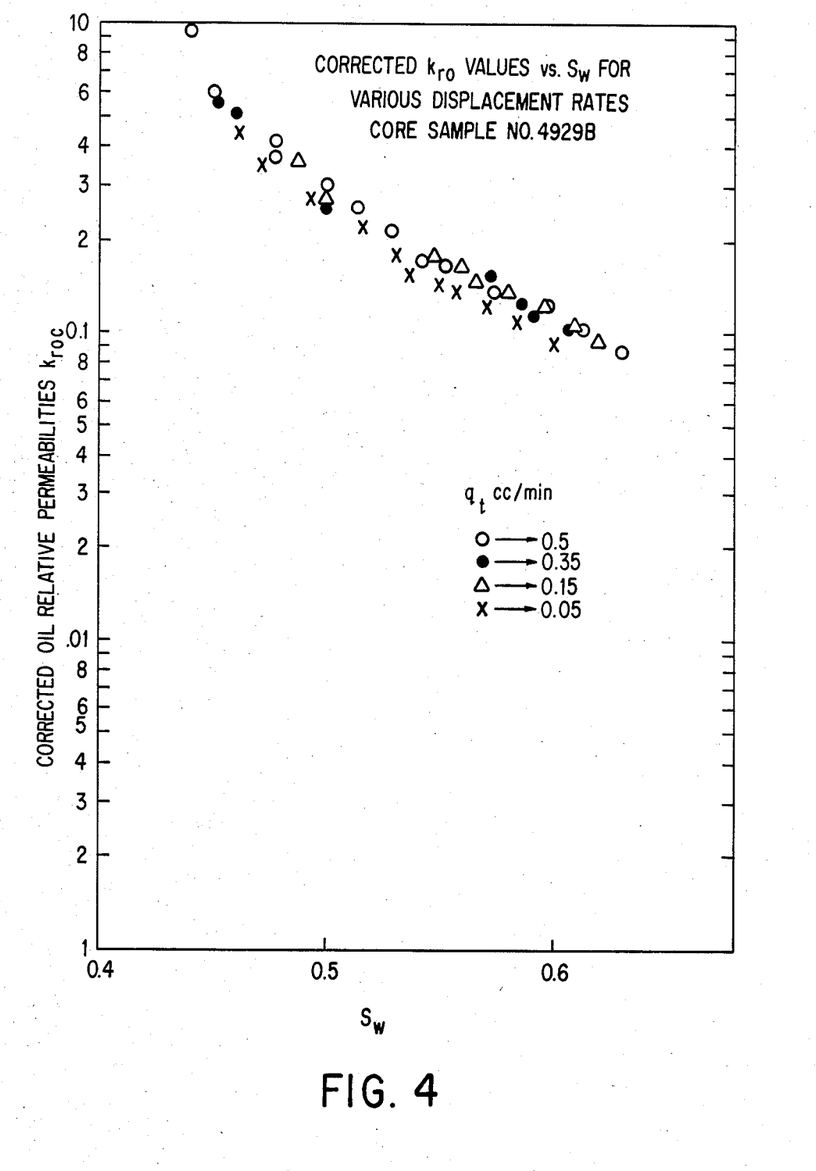
FIG. 4 are plots of corrected oil relative permeability values $k_{roc}$ vs. water saturation ($S_w$) for different displacement rates ($q_t$) for a first core sample using the method of the invention.
Figure 5:
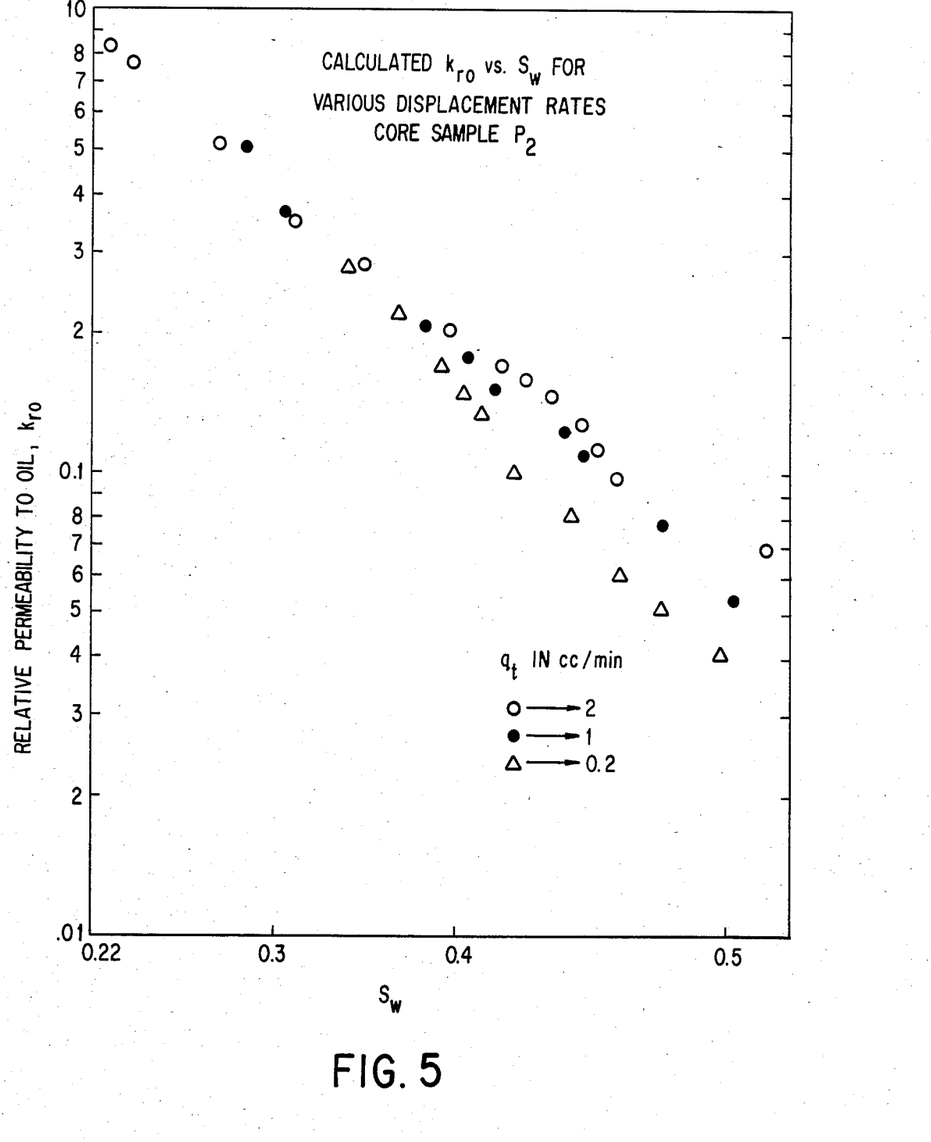
FIG. 5 are plots similar to those of FIG. 1, but for a second core sample.
Figure 6:
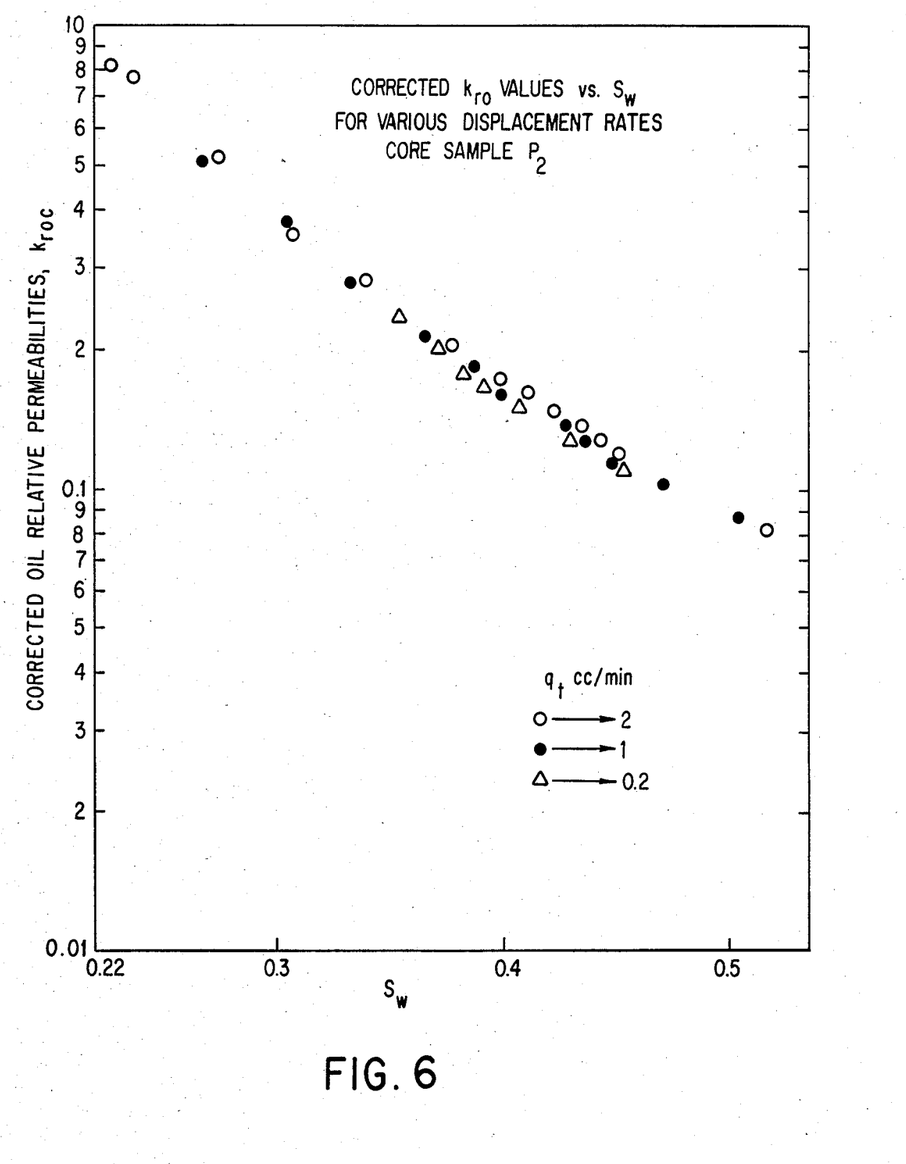
FIG. 6 are plots similar to those of FIG. 4, but for a second core sample.
Figure 7:
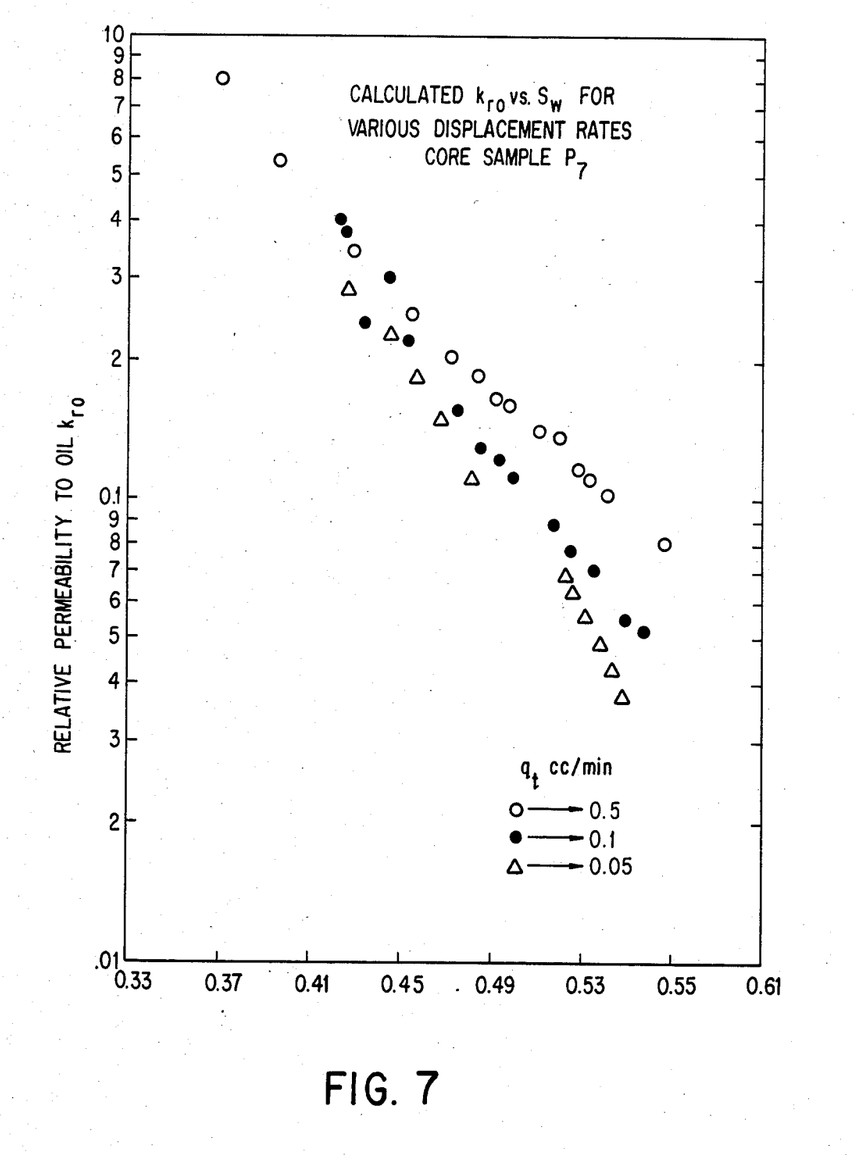
FIG. 7 are plots of calculated oil relative permeability values ($k_{ro}$) vs. water saturation ($S_w$) at various displacement rates ($q_t$) for a third core sample, produced using oil relative permeability values calculated in accordance with conventional techniques.
Figure 8:
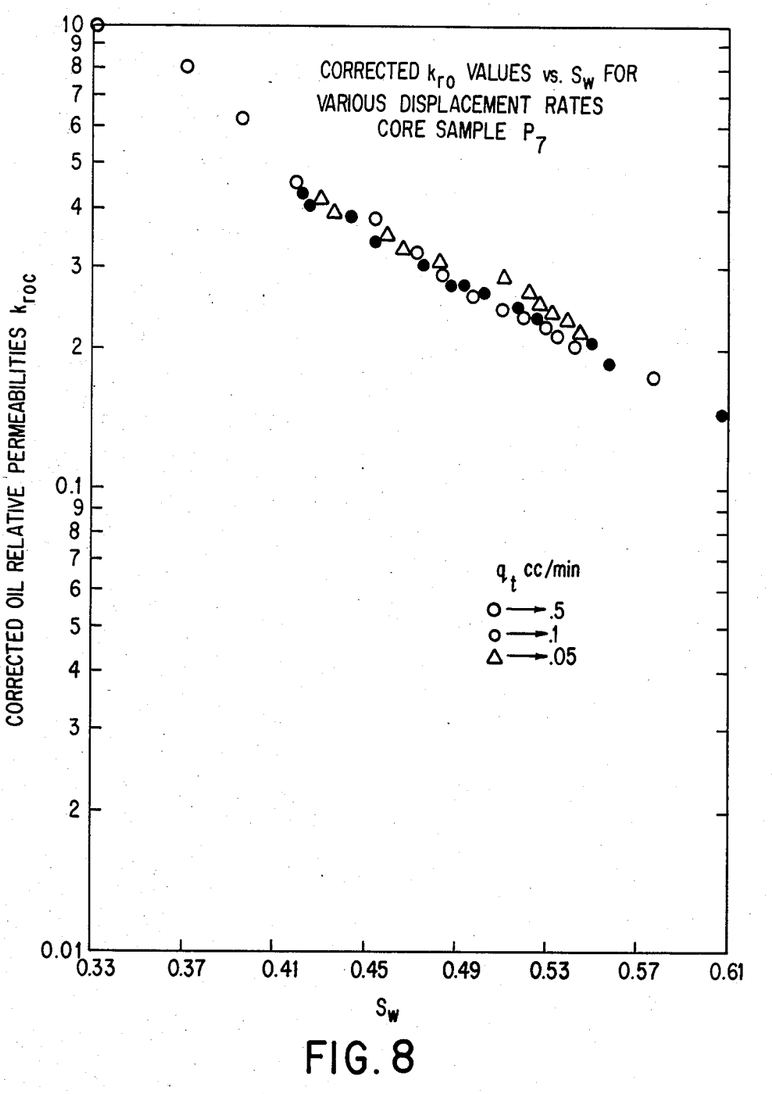
FIG. 8 are plots, similar to those of FIG. 7, but using oil relative permeability values ($k_{roc}$) corrected in accordance with the method of the invention.
Figure 9:
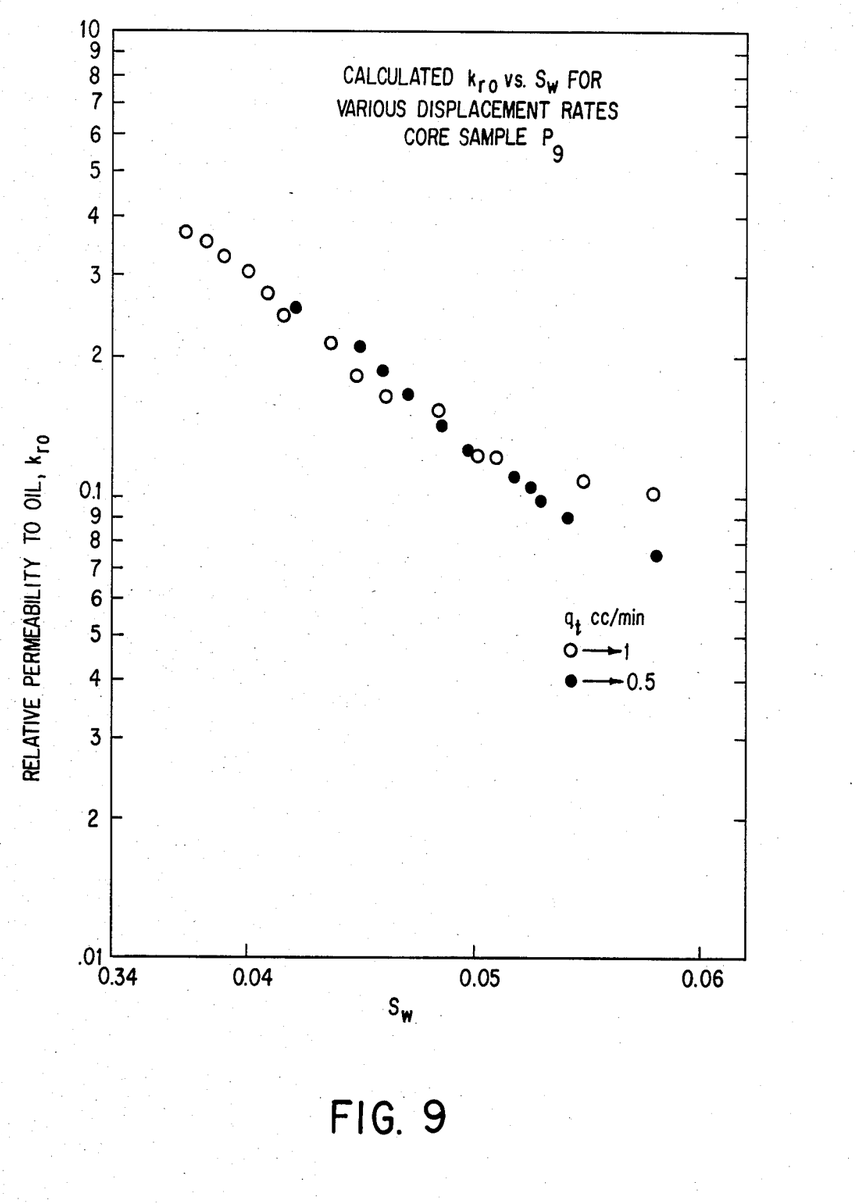
FIG. 9 are plots similar to those of FIG. 7, but for a fourth core sample.
Figure 10:
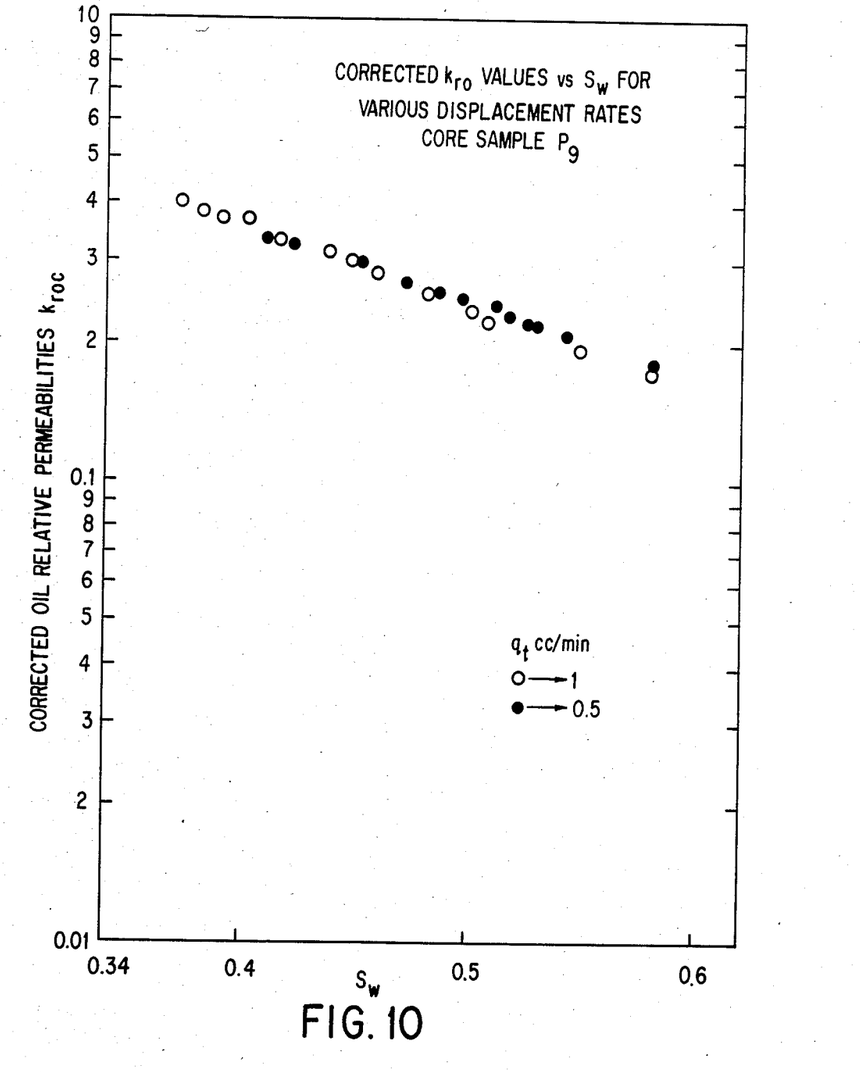
FIG. 10 are plots similar to those of FIG. 9, but using oil relative permeability values ($k_{roc}$) corrected in accordance with the method of the invention.

The method of the invention was used with several core samples to obtain corrected relative oil permeability values ($k_{roc}$). Dynamic displacement measurement data were collected on four core samples designated 4929B, $P_2$, $P_7$ and $P_9$. The permeabilities of these samples were respectively 25, 156, 31 and 695 millidarcies. Several displacement experiments with variations in flow rates as high as ten-fold were run on each core. Oil relative permeabilities were calculated using the conventional Jones and Roszelle technique, and plots of $k_{ro}$ vs. water saturation $S_w$ for different oil injection rates $q_t$ are depicted for the respective four core samples, as noted above, in FIGS. 1, 5, 7 and 9. The effect of flow rate on the calculated oil relative permeability values $k_{ro}$ is readily apparent from these figures. Thereafter, the method of the invention was employed, as graphically demonstrated in FIGS. 2 (straight line extrapolation) and 3 (tangent curve extrapolation) for the 4929B core sample, to correct the relative oil permeability values and the corrected results for the four core samples are respectively shown in the $k_{ro}$ vs. $S_w$ plots depicted in FIGS. 4, 6, 8 and 10. Except for a very low flow rate (0.05 cc/min) of core sample 4929B, the effective flow rate on the calculated $k_{ro}$ values has, for all practical purposes, been removed. The results of the 0.05 cc/min flood rate for the core sample 4929B are slightly below the other three, because no straight line developed for this case on the plot of $q_o/k_o$ vs. $\bar{S}_w$. Accordingly, correction was made by means of drawing a tangent, as illustrated in FIG. 2. Whenever a tangent curve is constructed, slight variations may be introduced in the plot which could result in the slight differences shown in FIG. 4.

It should be readily apparent to those skilled in the art that all procedures of the above-described method of the invention can be implemented by a suitably programmed digital computer. In addition, other variations can be made without departing from the spirit and scope of the invention. Accordingly, the invention is not limited by the foregoing description, but is only limited by the scope of the claims appended hereto.

I claim:

1. A method for determining correct relative oil permeability values for a core sample, comprising the steps of:

performing oil flood dynamic displacement measurements on said core sample;

determining characteristics of said core sample;

determining from data collected during said measurements, and from said characteristics of said core sample, relative oil permeability values ($k_{ro}$) for said core, said determined relative oil permeability values ($k_{ro}$) being offset from correct relative oil permeability values ($k_{roc}$) as a result of an end effect which introduces an increased fluid pressure drop at an effluent end of said core sample; and correcting said determined relative oil permeability ($k_{ro}$) values toward said correct relative oil permeability values ($k_{roc}$) thereby minimizing the effects caused by said end effect on said determined relative oil permeability values ($k_{ro}$), and wherein said correcting step comprises the steps of:

initially plotting a ratio $q_o/k_{ro}$ vs. average fluid saturation of said core sample, where $q_o$ is the rate of oil produced at the effluent end of said core sample during said oil flood dynamic displacement measurements;

determining an initial relative oil permeability value ($k_{roi}$) at a residual water saturation of said core sample, said value ($k_{roi}$) being used to determine the first point of the plot of $q_o/k_{ro}$ vs. average fluid saturation;

determining if a straight line segment exists in said plotted ratio in areas thereof corresponding to high oil saturation and, if so, drawing and extrapolating said straight line segment to the limit of the plotted data, otherwise, constructing a tangent curve to the plotted ratio beginning at the point corresponding to $k_{roi}$; and determining corrected relative permeability values $k_{roc}$, where $$k_{roc} = k_{ro} \frac{(q_o/k_{ro})}{(q_o/k_{ro})SL}$$

and $(q_o/k_{ro})$ is the initially plotted ratio and $(q_o/k_{ro})SL$ is the value appearing on the drawn and extrapolated straight line segment or the constructed tangent curve for the same average fluid saturation value.

2. A method as in claim 1, wherein said average fluid saturation is an average water saturation $(\bar{S}_w)$.

3. A method as in claim 1, wherein said average fluid saturation is an average oil saturation $(\bar{S}_o)$.

4. A method as in claim 1, wherein said initial relative oil permeability value ($k_{roi}$) is determined in accordance with Darcy's law.

5. A method, for determining correct relative oil permeability values for a core sample, comprising the steps of:

performing oil flood dynamic displacement measurements on said core sample;

determining characteristics of said core sample;

determining from data collected during said measurements, and from said characteristics of said core sample, relative oil permeability values ($k_{ro}$) for said core, said determined relative oil permeability values ($k_{ro}$) being offset from correct relative oil permeability values ($k_{roc}$) as a result of an end effect which introduces an increased fluid pressure drop at an effluent end of said core sample; and correcting said determined relative oil permeability ($k_{ro}$) values toward said correct relative oil permeability values ($k_{roc}$) thereby minimizing the effects caused by said end effect on said determined relative oil permeability values ($k_{ro}$), and wherein said determined relative oil permeability values ($k_{ro}$) are determined in accordance with the relationship $$k_{ro} = u_o f_o / \lambda_2^{-1}$$

where $u_o$ is the viscosity of the oil injected into said core sample during said oil flood measurements, $f_o$ is the fractional flow of oil from said core sample during said oil flood measurements and $\lambda_2^{-1}$ is the effective viscosity of the effluent at the outflow end of said core sample during said oil flood measurements.

6. A method for determining corrected oil relative permeability values for a core sample comprising the steps of:

injecting a first fluid through said core sample at a predetermined displacement rate for a first predetermined period of time and measuring: (1) a pressure drop of said fluid $\Delta Pb$ across said sample after a steady state flow is reached, and (2) a rate of injection of said fluid $q_b$ during said predetermined period of time;

determining the total amount of fluid injected Qi in terms of core pore volume;

injecting an oil through said core sample when said core sample is saturated with said fluid and during a second period of time while measuring a pressure drop $\Delta P$ across said sample;

determining a fractional oil flow $f_o$ for said core sample during said oil injection step;

determining average effective viscosity values $\bar{\lambda}^{-1}$ for the measured values of $\Delta P$, in accordance with the relationship:

$$\bar{\lambda}^{-1} = u_b \left( \frac{\Delta P}{q} \right) / \left( \frac{\Delta P_b}{q_b} \right)$$

where $u_b$ is the first fluid viscosity and $q$ is the oil injection rate;

determining effective viscosity values $\lambda_2^{-1}$, where $$\lambda_2^{-1} = \bar{\lambda}^{-1} - Q_i \frac{d\bar{\lambda}^{-1}}{dQ_i}$$

and $Q_i$ is the total amount of injected fluid in terms of core pore volume;

determining relative oil permeability values $k_{ro}$, where $$k_{ro} = u_o f_o / \lambda_2^{-1}$$

and $u_o$ is the viscosity of the oil injected into the core and $f_o$ is the fraction of oil produced at an effluent end of the core when oil is injected therein;

plotting the ratio $q_o/k_{ro}$ vs. average core saturation, where $q_o$ is the amount of oil contained in the effluent discharging from said core sample during said oil injection;

determining an initial relative oil permeability value $k_{roi}$ at the residual water saturation of the core sample, said value $k_{roi}$ being used to determine the first point of the $q_o/k_{ro}$ vs. average core saturation plot;

determining if a straight line segment exists in said plotted ratio in areas of the plot corresponding to high oil saturation and, if so, extrapolating said straight line segment to the limit of the plotted data, otherwise, constructing a tangent curve to the plotted ratio beginning at the point corresponding to $k_{roi}$; and determining corrected relative permeability values $k_{roc}$, where $$k_{roc} = k_{ro} \frac{(q_o/k_{ro})}{(q_o/k_{ro})SL}$$

and $(q_o/k_{ro})$ is the initially plotted ratio and $(q_o/k_{ro})SL$ is the value appearing on the drawn and extrapolated straight line segment or the constructed tangent curve for the same average saturation value.

7. A method as in claim 6, wherein said average core saturation comprises at least one of an average water ($S_w$) saturation and an average oil ($S_o$) saturation.

* * * * *